United States Patent [19]

Gull

[11] Patent Number: 4,764,517
[45] Date of Patent: Aug. 16, 1988

[54] 8α-(N,N-DIETHYLSULFAMOYLAMINO)-6-N-PROPYL ERGOLINE USEFUL AS A PROLACTIN SECRETION INHIBITOR, ANTI-PARKINSON, ANTI-DEPRESSANT AGENT

[75] Inventor: Peter Gull, Pfeffingen, Switzerland

[73] Assignee: Sandoz Ltd., Basel, Switzerland

[21] Appl. No.: 89,299

[22] Filed: Aug. 25, 1987

Related U.S. Application Data

[63] Continuation of Ser. No. 856,602, Apr. 25, 1986, abandoned, which is a continuation of Ser. No. 787,220, Oct. 15, 1985, abandoned, which is a continuation of Ser. No. 604,992, Apr. 27, 1984, abandoned, which is a continuation-in-part of Ser. No. 349,503, Feb. 17, 1982, abandoned, which is a continuation-in-part of Ser. No. 286,417, Jul. 24, 1981, abandoned.

[30] Foreign Application Priority Data

| Jul. 25, 1980 | [CH] | Switzerland | 5723/80 |
| Jul. 25, 1980 | [CH] | Switzerland | 5724/80 |
| Oct. 2, 1980 | [CH] | Switzerland | 7359/80 |
| Oct. 2, 1980 | [CH] | Switzerland | 7358/80 |
| Oct. 2, 1980 | [CH] | Switzerland | 7360/80 |

[51] Int. Cl.[4] .................... A61K 31/48; C07D 457/12
[52] U.S. Cl. .................................... 514/288; 546/68
[58] Field of Search ........................... 546/68; 514/288

[56] References Cited

U.S. PATENT DOCUMENTS

| 4,180,582 | 12/1979 | Kornfeld et al. | 546/67 |
| 4,202,279 | 5/1980 | Kornfeld et al. | 514/288 |
| 4,348,391 | 9/1982 | Stütz et al. | 546/68 |
| 4,348,392 | 9/1982 | Fehr et al. | 546/68 |
| 4,379,790 | 4/1983 | Horowski et al. | 546/68 |

FOREIGN PATENT DOCUMENTS

| 605938 | 10/1978 | Switzerland . |
| 1517971 | 7/1978 | United Kingdom . |
| 1567484 | 3/1980 | United Kingdom . |

OTHER PUBLICATIONS

Clemens et al., Chemical Regulation of Biological Mechanisms, pp. 167–180.
Fuller et al., Neuroendocrinology 36, 285–290, 1983.
Fuller et al., Endocrinolgy, vol. 109, No. 4, pp. 1026–1032, (1981).
Lemberger et al., Science, vol. 205, (1979), p. 1151.
Clemens et al., IRCS Medical Science: Biochemistry; Nervous System; Pharmacology; Psychology and Psychiatry 6, 427.
Nakamura et al., Communication in Psychopharmacology, vol. 3, pp. 179–183, (1979).

Primary Examiner—Robert Gerstl
Assistant Examiner—Cecilia Shen
Attorney, Agent, or Firm—Gerald D. Sharkin; Robert S. Honor; Thomas O. McGovern

[57] ABSTRACT

A compound of formula I

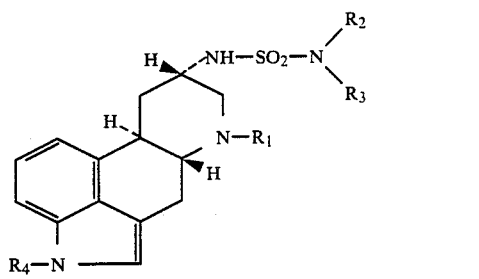

wherein
  $R_1$ is n-propyl,
  $R_2$ is hydrogen or alkyl($C_{1-3}$),
  $R_3$ is alkyl($C_{1-3}$), and
  $R_4$ is hydrogen or methyl in free base form or in pharmaceutically acceptable acid addition salt form is useful as a prolactin secretion inhibitor, anti-parkinson and anti-depressant agent.

6 Claims, No Drawings

8α-(N,N-DIETHYLSULFAMOYLAMINO)-6-N-PROPYL ERGOLINE USEFUL AS A PROLACTIN SECRETION INHIBITOR, ANTI-PARKINSON, ANTI-DEPRESSANT AGENT

This is a continuation of application Ser. No. 856,602, filed Apr. 25, 1986, now abandoned, which in turn is a continuation of application Ser. No. 787,220, filed Oct. 15, 1985, now abandoned, which in turn is a continuation of application Ser. No. 604,992, filed Apr. 27, 1984, now abandoned, which in turn is a continuation-in-part of application Ser. No. 349,503, filed Feb. 17, 1982, now abandoned, which in turn is a continuation-in-part of application Ser. No. 286,417, filed July 24, 1981, now abandoned.

This invention relates to ergoline derivatives, their production and pharmaceutical compositions containing them.

The present invention provides compounds of formula I

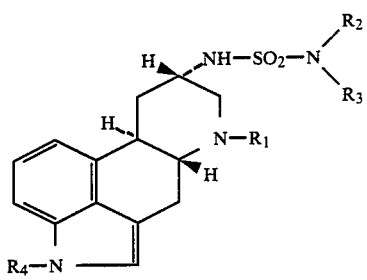

wherein
$R_1$ is n-propyl,
$R_2$ is hydrogen or alkyl($C_{1-3}$),
$R_3$ is alkyl($C_{1-3}$), and
$R_4$ is hydrogen or methyl.

Broad classes of ergolines, having prolactin secretion inhibition and dopaminergic activity, e.g. anti-parkinson activity and encompassing the present compounds of formula I wherein $R_4$ is hydrogen, have been published in the literature, for example Swiss patent No. 605938. In this Swiss patent it is specifically mentioned that the 6-position of the ergoline nucleus is preferably substituted by methyl or an α-branched alkyl radical such as isopropyl. All the characterised examples have a methyl group in the 6-position.

DOS No. 2656344 discloses a broad class of ergolines having the above-mentioned activities and encompassing the present compounds of formula I wherein $R_1$ is ethyl and $R_4$ is methyl. It is mentioned that the preferred substituent on the 6-position is methyl, and all the characterised examples have the 6-substituent as methyl.

None of the present compounds which have a n-propyl substituent in the 6-position of the ergoline nucleus have been, however, specifically disclosed or suggested by the literature, and it has been found that they have a very interesting pharmacological profile, and are particularly well tolerated and potent, e.g. as indicated the pharmacological tests mentioned hereinafter.

The present invention also provides a process for the production of a compound of formula I as defined above which includes the step of condensing a compound of formula II

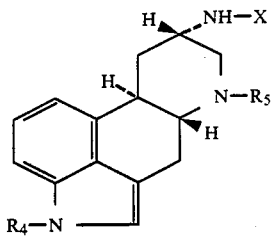

or a precursor thereof
with a compound of formula III $$Y-NR_2R_6 \quad \text{III}$$

or a precursor thereof
wherein
$R_2$ and $R_4$ are as defined above,
$R_5$ is hydrogen, or n-propyl,
$R_6$ is hydrogen or alkyl($C_{1-3}$),
and one of X and Y is $SO_2Z$ wherein Z is a leaving group, and the other of X and Y is hydrogen.

The reaction is preferably effected by reacting a compound of formula II wherein X is hydrogen with a compound of formula IV $$Z-SO_2-NR_2R_6$$

wherein $R_2$ and $R_6$ and Z are as defined above.

The reaction may be effected in conventional manner for the production of analogous compounds. Z is preferably chlorine or bromine. Suitable solvents include, for example, appropriate chlorinated aliphatic hydrocarbons such as methylene chloride or chloroform or appropriate cyclic or open chain ethers such as dioxane. Suitable reaction temperatures may be between about −10° and about 80° C.

The compound of formula II and/or III may be used in the form of a precursor, e.g. in protected form and then deprotected later. The protecting group may for example be attached to a nitrogen atom and may for example be an aminoprotecting group.

Naturally if $R_5$ or $R_6$ is hydrogen, then a subsequent alkylation is necessary to produce a compound of formula I. Besides the alkylation in position 1 or 6 of the ergoline nucleus, the sulfamoyl group may be easily alkylated.

Any desired further conversion, e.g. alkylation, may be effected in conventional manner. The type, amounts of alkylating agents used, and reaction conditions may naturally be chosen, if desired, along with temporary protection of amine groups, to effect alkylation selectively in position 1 or 6, or effect mono- or dialkylation in the sulfamoyl group.

An alkylation in position 1 or 6 of the ergoline nucleus may be, for example, effected by reaction of the corresponding compound unsubstituted in position 1 or 6 with a compound of formula $CH_3-Z$ or $C_2H_5-Z$ (for the $R_4$=ethyl compounds)
and/or $R_1-Z$ wherein $R_1$ is as defined above and Z is a leaving group, e.g. halogen of atomic number 9 to 53 or an organic sulphonic acid radical e.g. tosyloxy.

The reaction is preferably effected in an inert organic solvent, conveniently at temperatures of between about 10° and about 100° C. and suitably in the presence of a base. The alkylation in position 6 may alternatively be effected under reductive conditions, e.g. by catalytic hydrogenation under mild reaction conditions.

Alkylation on the sulfamoyl nitrogen may be effected in conventional manner for alkylation of amines. Naturally it is to be appreciated that when $R_4$ or $R_5$ in the starting material is hydrogen then these positions may be alkylated first.

The reaction is preferably effected with an alkyl halide in acetone, dimethylformamide or a chlorinated hydrocarbon in the presence of a base. If a mono-alkylation on the sulfamoylamino nitrogen atom is required (and if desired alkylation in positions 1 or 6 of the ergoline nuleus) the alkyl halide is preferably used in at most equivalent amounts based on the ergoline starting material. If a dialkylation of the sulfamoylamino nitrogen is required then the alkyl halide is preferably used in excess.

The compounds of formula I may be isolated and purified in conventional manner.

Free base forms of the compounds of formula I may be converted into acid addition salt forms in conventional manner and vice versa. Suitable acids for salt formation include for example hydrochloric acid, sulphuric acid, maleic acid, fumaric acid and tartaric acid.

Compounds of formula II wherein X is $SO_2Z$ may be obtained by introducing the group $SO_2Z$ into the corresponding compounds of formula II wherein X is hydrogen. When Z is chlorine this may be effected for example by reacting a compound of formula II wherein X is hydrogen with sulphuryl chloride, if necessary with temporary protection of the nitrogen atom in positions 1 or 6 of the ergoline nucleus when $R_4$ or $R_5$ is hydrogen.

Some of the compounds of formula II wherein X is hydrogen are new, for example, compounds of formula II wherein X is hydrogen, $R_4$ is hydrogen or methyl and $R_5$ is hydrogen and compounds of formula II wherein X is hydrogen, $R_4$ is methyl and $R_5$ is n-propyl. All the compounds of formula II wherein X is hydrogen may be produced in conventional manner from 8α-amino-6-methyl-ergoline. Thus the 8α-amino group may be protected by e.g. benzyloxycarbonyl. The 6-methyl group can then be replaced by a group $R_1$ and the 1 position may be methylated.

Insofar as the production of any starting material is not particularly described, these are known or may be produced in conventional manner.

In the following examples all temperatures are in degrees Centigrade and are uncorrected.

All optical rotations were made at the sodium D line.

EXAMPLE 1:

8α-(N,N-diethylsulfamoylamino)-6-n-propylergoline

[Alternative nomenclature
N,N-diethyl-N'-(6-n-propylergolin-8α-yl)sulfamide]

A solution of 2 ml (ca 26 mM) diethylsulfaminic acid chloride in 5 ml chloroform is added dropwise to a refluxing solution of 2.2 g (8.2 mM) 8α-amino-6-n-propyl-ergoline in 50 ml chloroform and 5 ml triethylamine. The mixture is refluxed for 12 hours, and then cooled to room temperature. 10 ml of 2N sodium hydroxide are added and the mixture is stirred for 1 hour at room temperature. To work up, extration is effected three times with methylene chloride/isopropanol (9:1). The combined organic phases are dried with sodium sulphate, filtered and concentrated to yield the title compound.

The hydrochloride salt form is recrystallized from ethanol/methylene chloride (1:1). M.pt. 160°-162°; $[\alpha]^{20} = -56°$ [c=0.4 in ethanol/water (1:1)].

The ergoline starting material may be obtained as follows:

(a) 8α-benzyloxycarbonylamino-6-methylergoline 10.5 ml (75 mM) carbobenzyloxychloride are added to a suspension of 18 g (74.7 mM) 8α-amino-6-methylergoline in 1000 ml chloroform, 150 ml isopropanol and 37 ml 2N (74 mM) sodium hydroxide at room temperature. The mixture is stirred for 2 hours at room temperature. After separation of the organic phase, this is dried, filtered and concentrated. The resultant crude product is filtered through silicagel with methylene chloride/methanol (99:1) giving the heading compound as a foam.

(b) 8α-benzyloxycarbonylamino-6-cyanoergoline

A solution of 29.5 g (79 mM) of 8α-benzyloxycarbonylamino-6-methylergoline obtained from step (a) and 25 g (236 mM) cyanobromide in 600 ml chloroform is stirred for 65 hours at room temperature and finally concentrated on a rotary evaporator to give the heading compound which is dried in a high vacuum.

(c) 8α-benzyloxycarbonylaminoergoline 18 g (46.5 mM) of 8α-benzyloxycarbonylamino-6-cyanoergoline obtained from step (b) in 100 ml acetic acid are added to a suspension of 40 g zinc in 100 ml acetic acid. 40 ml water are added and the mixture is heated at 100° for 10 hours. To work up, the mixture is filtered through a filtering aid such as Hyflo and concentrated in a rotary evaporator. The residue is partitioned between potassium bicarbonate aqueous solution and methylene chloride/isopropanol (b 9:1). The organic phase is dried over sodium sulphate, filtered and concentrated to give the heading compound in crude form.

(d) 8α-benzyloxycarbonylamino-6-n-propylergoline

A suspension of 17.5 g (ca. 46 mM) of 8α-benzyloxycarbonylaminoergoline obtained from step (c), 13.5 g potassium carbonate and 6 ml (62 mM) n-propyl iodide in 300 ml dimethylformamide is stirred for 18 hours at room temperature. The mixture is filtered and concentrated in a rotary evaporator. The residue is treated with methylene chloride and shaken with water. The organic phase is dried over sodium sulphate, filtered and concentrated to give the crude heading compound.

(e) 8α-amino-6-n-propylergoline 12 g (ca 30 mM) of 8α-benzyloxycarbonylamino)-6-n-propylergoline obtained from step (d) and 1.5 g palladium on charcoal (10% by weight) in 500 ml ethanol are hydrogenated at normal pressure until hydrogen uptake ceases. The mixture is filtered and concentrated. This resultant heading compound is crystallised from methanol.

In analogous manner to that described in Example 1 the following compound of formula I are obtained by reacting the appropriate compound of formula II and a compound of formula III, wherein X is H and Y is $ClSO_2$:

EXAMPLE 2:
1-methyl-8α-(N,N-dimethylsulfamoylamino)-6-n-propylergoline

Hydrochloride salt: M.pt. from 220° decomp.; $[\alpha]_D^{20} = -65°$ [c=0.445 in ethanol/water (1:1)].

EXAMPLE 3:
8α-(N,N-dimethylsulfamoylamino)-6-n-propylergoline

Hydrochloride salt: M.pt. from 220° decomp.; $[\alpha]_D^{20} = -63°$ [c=0.43 in ethanol/water (1:1)].

EXAMPLE 4:
8α-(N,N-diethylsulfamoylamino)-1-methyl-6-n-propylergoline

Hydrogen fumarate salt: M.pt. from 180° decomp.; $[\alpha]_D^{20} = -31.5°$ [c=0.96 in pyridine].

EXAMPLE 5:
8α-(N-methylsulfamoylamino)-6-n-propylergoline

Free base: 103°–107° (m.pt)

EXAMPLE 6:
8α-(N,N-diethylsulfamoylamino)-6-n-propylergoline 76.7 g 8α-amino-6-propylergoline in 592 ml methylene chloride and 104 ml methanol are stirred at room temperature. 202 ml triethylamine is added over 10 minutes and the temperature maintained below 25°. The suspension is treated with 123 ml diethylsulfamoyl chloride and the mixture stirred for 16 hours.

250 ml concentrated ammonia is added as well as 250 ml water over 15 minutes. The mixture is stirred for another 3 hours and partitioned. The aqueous layer is extracted with methylene chloride (350 ml) and methanol (70 ml). The combined organic phases are washed with sodium hydroxide, water and brine and treated with active charcoal, filtered through a filtering aid such as HYFLO and concentrated to 350 ml. The resultant mixture is diluted with 350 ml methanol and reduced in volume to 350 ml under a vacuum. The mixture is cooled to 0° and the title compound crystallizes out.

The starting material may also be produced as follows:

(a) 17.9 g 6-n-propyl-8α-ergoline hydrazide (known from A. Cerny et al Coll. Czech. Chem. Commun Vol. 48, 1483 (1983)) are added to 315 ml hydrochloric acid. The mixture is stirred at pH 2–3 for 5 minutes, cooled to 0° to 5° and a solution of 308 ml and 0.2N sodium nitrite is added at 0° to 5° over 15 minutes. 350 ml 2N hydrochloric acid are added. The mixture containing the corresponding ergoline azide is stirred for 15 minutes. 10 ml of 10% aminosulphonic acid solution are added.

(b) In a 2.5 liter vessel 260 ml 0.4N hydrochloric acid is warmed to 80°. The azide reaction mixture from (a) is added over 40 to 45 minutes at such a rate that the temperature remains at 80° (Nitrogen is produced upon azide decomposition). The mixture is stirred for 30 minutes and then cooled to 20°–25°.

30 ml of concentrated sodium hydroxide solution (pH>11) are added over 15–30 minutes and the precipitated suspension filtered off, washed and dried to give crude 8α-amino-6-n-propyl-amino-ergoline.

The crude product is dissolved in 300 ml methylene chloride/ethanol (1:1), reduced in volume to about 80 ml and then 50 ml ethanol is added. 50 ml of solvent is removed under vacuum and then the mixture is stirred at 0° C. to give 8α-amino-6-n-propyl-ergoline.

The compounds of formula I have not been described in the literature.

The compounds of formula I are useful because they possess pharmacological activity in animals. In particular, the compounds of formula I are useful in prolactin secretion inhibition agents, as indicated by an inhibition of the implantation of fertilized eggs in the uterus on day 5 after insemination of female rats administration of from about 0.001 to about 0.1 mg/kg s.c. of the compounds [according to the principles of Experienta 34, 1330, (1978)].

In particular prolactin secretion activity of the compounds is determined in the following tests with the Example 1 and 4 compounds:

Implantation inhibition

Adult proestrus rats (Ivanovas strain) were brought together with males of proven fertility. The next morning (day 1) the sperm positive females were randomly allocated to the different treatment groups (10 animals per group). On day 5 a single dose of the substance was injected s.c.

The rats were killed on day 12 and autopsied. The uteri were inspected for foetuses or implantation sites arising from fertilized eggs. If none were found then ovum implantation was said to have been inhibited. Thus the results were of the all or none type. The dose required to inhibit implantation in 50% of the animals was calculated ($ED_{50}$). Example 1 compound 0.007 mg/kg; Example 4 compound 0.022 mg/kg.

Lactation inhibition

Groups of 5 to 6 lactating female rats (Invanovas strain) were given daily oral doses of the substance or vehicle from day 5 to day 8 post partum and the regression coefficients to the growth rates of the pups were calculated taking the daily weight gain of the young as indication of milk yield. The dose of substance reducing lactation to half the control amount was calculated ($ID_{50}$). Example 1 compound 0.01 mg/kg p.o.. Example 2 compound 0.02 mg/kg p.o.

On the basis of their prolactin secretion inhibition effect the compounds of formula I are useful for the treatment of endocrinological indications associated with prolactin secretion, e.g. galactorrhoea, amenorrhoea, prolactin-dependent menstrual disorders and subfertility, inhibition of lactation, incipient puerperal mastitis, post-partum puerperal mastitis, post-partum mammary congestion, prolactin-dependent pre-menstrual symptoms, acromegaly and prolactin-dependent male hypogonadism and impotence and oligospermia.

For the above mentioned use the dosage will, of course, vary depending on the compound employed, mode of administration and therapy desired. However, in general, satisfactory results are obtained when administered at a daily dosage of from 0.001 mg to about 0.5 mg per kg animal body weight, conveniently given in divided doses 2 to 4 times a day or in sustained release form. For the larger mammal, the total daily dosage is in the range from about 0.01 to about 1 mg, and dosage forms suitable for oral administration comprise from about 0.003 to about 0.5 (e.g. 0.003 to 0.3) mg of the compounds admixed with a solid or liquid pharmaceutical carrier or diluent.

Additionally, the compounds of formula I are useful as anti-parkinson agents, e.g. for the treatment of Morbus Parkinson as indicated by an induction of contralateral turning in rats with a unilateral 6-hydroxydopamine-induced degeneration of the nigroneostriatalen dopamine pathway at doses of about 0.01 to about 2 mg/kg p.o. and i.p. [according to the principles of U. Ungerstedt, Act. physiol. Scand. Suppl. 367, 69–93, (1971)].

In particular the compounds of Examples 1 and 4 are tested as follows:

Under pentobarbital (NEMBUTAL) anesthesia, male OFA rats (140–160 g) were placed in a David-Kopf stereotaxic frame. A sagittal cut was made in the skin and the underlying tissue scraped to expose the bregma. A 2 mm wide aperture was drilled +4.2 mm anterior and 1 mm lateral (right) from the bregma, and a cannula with 0.3 mm external diameter (2R2 No. 3 cardiac needle) was inserted 7.5 mm deep from the dura. A 4-$\mu$l solution of 6-hydroxydopamine hydrochloride (2 mg/ml 6-OHDA in saline with 0.2 mg/ml ascorbic acid as an antioxidant) was injected into the medial substantia nigra over 2 min period with the aid of a Hamilton syringe driven by an "Agla" micrometer gauge. The cannula was then withdrawn and the wound closen with clips. I week later the animals were challenged with 0.25 mg/kg s.c. apomorphine and the total number of rotations were measured. Animals responding by turning contralaterally to the side of the lesions were selected for further experiments. To facilitate comparison between different compounds and between different groups of animals, the number of rotations in each animal were corrected by a factor derived from the mean value of 560 total turns per animal obtained from 40 rats injected with 0.25 mg/kg i.p. apomophine. Animals were used at the earliest 4 weeks after lesioning and subsequently received no more than one treatment per week. The registration of turning was carried out by observation and with the aid of a manual counter. The direction of turns was recorded in all instances.

The total number of revolutions, the duration of effect and maximal intensity per minute were determined: Groups of at least 3 animals were used.

Central dopaminergic effect

The selectivity of the dopaminergic effect is determined by the measuring the indication of stereotypy in the rat according to the standard tests:

Male OFA rats (180 to 250 g) were placed in perspex cylinders of 23 cm diameter with a wire grid floor. After 30 minutes to allow familiarization to the cage, the animals were injected subcutaneously with 30 mg/kg i.p. of the compounds and observed at 30 minutes intervals for 2 h and then at 60 minutes intervals for a total of 7 h. 6 rats were investigated at each dose level. The degree of stereotyped behaviour was assessed using a scoring system based on that described by Costalt et al. Eur. J. Pharmacol. (1972), 18, 83. The scores and criteria were as follows:

(1) intermittent sniffing of moderate intensity;
(2) persistent sniffing, occasional licking;
(3) marked licking, occasional to moderate biting;
(4) intense and persistent biting.

A high score indicates central action of the compounds.

| Example | Dose | Score | Duration (hours) |
|---------|------|-------|------------------|
| 1 | 1 ip | 14.3 | 6 |
| 1 | 3 ip | 15.0 | 6 |
| 4 | 30 ip | 12.0 | 6 |

For this use the dosage will, of course, vary depending on the compound employed, mode of administration and therapy desired. However, in general, satisfactory results are obtained when administered at a daily dosage of from about 0.01 to about 5 (e.g. 0.1 to 5) mg per kg animal body weight, conveniently given in divided doses 2 to 4 times a day or in sustained release form. For the larger mammal, the total daily dosage is in the range from about 0.5 to about 10 mg, and dosage forms suitable for oral administration comprise from about 0.15 mg to about 5 mg of the compounds admixed with a solid or liquid pharmaceutical carrier or diluent.

Furthermore, the compounds are useful as antidepressant agents as indicated in animal tests, e.g. an antagonism of reserpine-induced catalepsy and ptosis is observed at doses of from about 0.01 to about 0.1 mg/kg s.c..

Anti-depressant activity (Example 1 and 4 compounds)

The anti-depressant activity of the compounds was determined in conventional manner by measuring the ability of the compounds to inhibit resperine induced akinesia and ptosis in mice. The method is essentially the same as that described by J. M. Vigouret et al., Pharmacology 26 (Suppl. 1), 156–173 (1978) as follows:

Male MNRI mice (18–25 g) in groups of 10 were injected with reserpine, 5 mg/kg i.p., 17 h before subcutaneous administration of the compounds under investigation (duration of reserpine-induced akinesia and ptosis 24 h). Akinesia and ptosis was assessed at 0.5, 1, 2, 3 and 5 h after administration of test substances. The number of mice exhibiting antagonism of akinesia, i.e. which were able to walk off a twine-covered vertical pole in a coordinated manner, was recorded. At each dose level and at each time period the percentage antagonism of akinesia was calculated by comparison of the responses of control (reserpine only) to the experimental (reserpine and compound) animals. Ptosis was also assessed in conventional manner according to a scoring system depending on the extent the eyelids were closed. The $ED_{50}$ was determined with at least three doses of each compound for each observation time.

$ED_{50}$ (5 hours) Catalepsy Example 1 compound 0.11 mg/kg

Example 4 compound 0.17 mg/kg

Ptosis Example 1 compound 0.14 mg/kg

For this use the dosage will, of course, vary depending on the compound employed, mode of administration and treatment desired. However, in general, satisfactory results are obtained when administered at a daily dosage of from about 0.01 to about 0.5 mg per kg animal body weight, conveniently given in divided doses 2 to 4 times a day or in sutained release form. For the larger mammal, the total daily dosage is in the range from about 1 to about 10 mg, and dosage forms suitable for oral administration comprise from about 0.5 mg to about 5 mg of the compounds admixed with a solid or liquid pharmaceutical carrier or diluent.

The Example 1 compound exhibits activity in the above prolactin inhibition test at doses of about 0.005 mg/kg s.c.; in the above anti-parkinson test at doses of about 0.1 mg/kg i.p. and in the above anti-depressant test in doses of about 0.01 mg/kg s.c.

The Example 1 compound is the preferred compound.

The invention also includes compounds for use in the above-mentioned indications, i.e. prolactin secretion inhibition, Morbus Parkinson and depression.

The compounds of formula I may be administered in similar manner to known standards for use in the utilities, for example, bromocriptine. The suitably daily dose for a particular compound will depend on a number of factors such as its relative potency of activity. It has for example been determined that the preferred compound of this invention, the Example 1 compound, has an $ED_{50}$ of 0.007 mg/kg s.c. in the above mentioned implantation test for prolactin secretion inhibition activity as compared to an $ED_{50}$ of 0.75 mg/kg s.c. for bromocriptine in this test. In the Ungerstedt test for anti-parkinson activity the Example 1 compound provokes about 1500 rotations on administration of 0.1 mg/kg i.p as compared to about 80 rotations provoked by bromocriptine at a dose of about 0.1 mg/kg s.c. It is therefore indicated that the Example 1 compound may be administered at at least ten times lower dosages than bromocriptine in the prolactin secretion inhibition and anti-parkinson indications.

A proposed daily dosage for the Example 1 compound is from 0.1 to 0.2 mg p.o. for the larger mammal as a prolactin secretion inhibitor and from 1 to 2 mg p.o. for the larger mammal as an anti-parkinson agent. The compounds may be administered in the form of a pharmaceutically acceptable acid addition salt. Such salt forms have the same order of activity as the free base form. The present invention accordingly provides a compound of formula I in free base form or in pharmaceutically acceptable acid addition salt form in association with a pharmaceutical carrier or diluent. Such compositions may be formulated in conventional manner conveniently under the exclusion of light so as to be, for example, a solution capsule or a tablet.

Suitable capsule formulations include:

|  | mg | mg | mg |
|---|---|---|---|
| Example 1 compound (HCl salt) | 0.109 | 0.0218 | 0.00545 |
| Mannitol | 0.891 | 9.9782 | 9.99455 |
| Lactose (200 mesh) | 165.5 | 165.5 | 165.5 |
| Corn Starch | 120.0 | 120.0 | 120.0 |
| Silica (Aerosil 200) | 1.5 | 1.5 | 1.5 |
| Magnesium stearate | 3.0 | 3.0 | 3.0 |
| in capsule | 300 mg 78 mg | 300 mg | 300 mg |

In a group of compounds $R_1$ is n-propyl and $R_4$ is methyl.

What we claim is:

1. 8α-(N,N-diethylsulfamoylamino)-6-n-propylergoline in free base form or in pharmaceutically acceptable acid addition salt form.

2. A pharmaceutical composition which comprises a compound of claim 1 in free base form or in pharmaceutically acceptable acid addition salt form in association with a pharmaceutically carrier or diluent.

3. A method of inhibiting prolactin secretion in a subject in need of said treatment which comprises administering a therapeutically effective amount of a compound of claim 1 to a subject in need of such treatment.

4. A method of treating Morbus Parkinson in a subject in need of said treatment which comprises administering a therapeutically effective amount of a compound of claim 1 to a subject in need of such treatment.

5. A method of treating depression in a subject in need of said treatment which comprises administering a therapeutically effective amount of a compound of claim 1 to a subject in need of such treatment.

6. The compound of claim 1 which is the hydrochloride salt of 8-(N,N-diethylsulfamoylamino)-6-n-propylergoline.

* * * * *